United States Patent [19]

Tateosian et al.

[11] Patent Number: 4,615,665

[45] Date of Patent: Oct. 7, 1986

[54] METHOD FOR MAKING DENTAL PROSTHETIC DEVICE WITH OXYGEN BARRIER LAYER AND VISIBLE LIGHT IRRADIATION TO CURE POLYMER

[75] Inventors: Louis H. Tateosian; Shek C. Horne, both of York, Pa.

[73] Assignee: Dentsply International Inc., York, Pa.

[21] Appl. No.: 492,441

[22] Filed: May 6, 1983

[51] Int. Cl.[4] ............................................. B29C 71/04
[52] U.S. Cl. ...................................... 425/16; 264/22; 264/129
[58] Field of Search ...................... 427/54.1, 154–156, 427/160, 44; 264/16, 17, 22; 433/167, 199; 427/44; 204/159.15, 159.23

[56] References Cited

U.S. PATENT DOCUMENTS

| | | | |
|---|---|---|---|
| 2,341,604 | 2/1944 | Dresch | 264/17 |
| 2,472,492 | 6/1949 | Saffir | 156/293 |
| 3,060,026 | 10/1962 | Heiart . | |
| 3,277,009 | 10/1966 | Freifeld et al. | 427/155 |
| 3,458,311 | 7/1969 | Alles | 430/273 |
| 3,544,349 | 12/1970 | Isaksen et al. | 427/156 |
| 3,709,866 | 1/1973 | Waller | 523/115 |
| 3,753,715 | 8/1973 | Klupfel et al. . | |
| 3,804,631 | 4/1974 | Faust . | |
| 4,016,306 | 4/1977 | Miyagawa et al. | 427/54.1 |
| 4,051,302 | 9/1977 | Mayama et al. | 427/54.1 |
| 4,071,424 | 1/1978 | Dart et al. | 204/159.15 |
| 4,072,528 | 2/1978 | Bratt | 430/556 |
| 4,089,763 | 5/1978 | Dart et al. | 204/159.23 |
| 4,110,184 | 8/1978 | Dart et al. . | |
| 4,200,463 | 4/1980 | Flowers . | |
| 4,218,294 | 8/1980 | Brack . | |
| 4,245,031 | 1/1981 | Chambers | 430/288 |
| 4,267,133 | 5/1981 | Kohmura et al. | 264/22 |
| 4,268,611 | 6/1981 | Okishi et al. . | |
| 4,323,591 | 4/1982 | Wendling et al. . | |
| 4,388,069 | 6/1983 | Orlowski | 204/159.23 |
| 4,396,476 | 8/1983 | Roemer et al. . | |
| 4,411,625 | 10/1983 | Kobutz et al. | 204/159.23 |
| 4,416,975 | 11/1983 | Green et al. | 204/159.22 |
| 4,421,782 | 12/1983 | Bolgiano et al. | 264/22 |
| 4,458,007 | 7/1984 | Geissler et al. | 204/159.23 |
| 4,500,657 | 2/1985 | Kumar | 204/159.23 |

FOREIGN PATENT DOCUMENTS

| | | |
|---|---|---|
| 0018765 | 12/1980 | European Pat. Off. . |
| 3316591 | 10/1984 | European Pat. Off. . |
| 3330853 | 3/1985 | Fed. Rep. of Germany . |
| 51-109937 | 3/1975 | Japan . |

OTHER PUBLICATIONS

Chemical Abstracts, vol. 88, No. 24, 6/12/78, p. 24.
Chemical Abstracts, vol. 90, No. 18, 5/30/79, p. 4.
Ruyter, I. E. Unpolymerized Surface Layers on Sealants, Acta Odontol. Scand. 1981, 39, 27–32.

*Primary Examiner*—Willard E. Hoag
*Attorney, Agent, or Firm*—Edward J. Hanson, Jr.

[57] ABSTRACT

The present invention provides a new method of ameliorating oxygen inhibition especially with curable dental material having a polymerizable system including polymerizable organic compound, and polymerization initiator activatable by actinic radiation. The method involves shaping the dental material into a shaped member having relatively vertical surface and relatively horizontal surface, preparing a liquid composition, applying the liquid composition to the relatively vertical surface and the relatively horizontal surface to the member, forming a layer from the liquid composition, and applying actinic light to the light curable material through the layer. The method preferably involves including water and organic compound in the liquid composition and providing the layer in an amount of at least about 35 mg/dm$^2$ on a fully dried weight basis.

7 Claims, No Drawings

METHOD FOR MAKING DENTAL PROSTHETIC DEVICE WITH OXYGEN BARRIER LAYER AND VISIBLE LIGHT IRRADIATION TO CURE POLYMER

BACKGROUND OF THE INVENTION

The present invention relates to protecting polymerizable materials from interference from surrounding air during curing by providing a barrier over the curable material.

For many years it has been known that the oxygen in the air of the normal ambient environment interferes with the curing of polymerizable materials by what is reported as oxygen inhibition. By this it is understood that the oxygen present in the air retards or even prevents the polymerization of the compositions and particularly at their surface interface with the air. In general, the surfaces of unprotected surfaces remain tacky because of incomplete polymerization of the resins and the surface remains weak and subject to leeching and other deleterious action.

U.S. Pat. No. 3,458,311 reveals a photopolymerizable stratum that is protected by an adherent solid protective stratum present in an amount of 2 to 30 mg/dm$^2$ made from a mixture of hydrophilic water soluble polymers such as those shown in Column 2 including polyvinyl pyrrolidone and polyvinyl alcohol and a surfactant in water. Optionally a chain transfer agent may by present as taught in Column 2 Line 32.

U.S. Pat. No. 4,072,528 also reveals a photopolymerizable element having a support and in addition a polymerizable photosensitive layer on the support and a solid water permeable oxygen barrier protective layer over the polymerizable photosensitive layer. The protective layer is applied as a coating from an aqueous solution of a water soluble macromolecular organic copolymer such as polyvinyl alcohol having disbursed therein finely divided solid particles of a water insoluble chlorinated vinyl copolymer.

It is an object of the present invention to provide a surface cure promoting coating that overcomes the deficiencies of the prior art.

It is a further object of the present invention to provide a curing of polymerizable compositions that is adequate to withstand use in long term application in the oral environment of the human mouth.

By yet another object of the present invention it is desired to provide a rapid rate of cure to a substantial depth and at the same time provide a surface that is non-tacky and resistant to acids and bases; and resistant to staining, fouling, odor sorption and blanching and has good durability or weatherability and a glossy surface.

An additional object of the invention is to provide a liquid composition that enables vertical surfaces to be coated with a substantially thick coating that is fluid enough to assure an uninterrupted non-leaking surface.

Another object of the invention is to use a material that will not cause a toxic end product.

Another object of the invention is to provide an economical method of curing polymerizable materials.

SUMMARY OF THE INVENTION

By the present invention in one aspect a method of ameliorating oxygen inhibition with curable dental material is provided for use with a polymerizable system including polymerizable organic compound, and polymerization initiator activatable by actinic radiation. The method involves shaping the dental material into a shaped member having relatively vertical surface and relatively horizontal surface, preparing a liquid composition, applying the liquid composition to the relatively vertical surface and the relatively horizontal surface of the member, forming a layer from the liquid composition, and applying actinic light to the light curable material through the layer. The method preferably involves including water and organic compound in the liquid composition and providing the layer in an amount of at least about 35 mg/dm$^2$ on a fully dried weight basis.

By another aspect of the invention a photopolymerizable element is provided containing the previously described substrate and a protective stratum substantially transparent to actinic radiation over at least a portion of the substrate the layer present in an amount of at least about 35 mg/dm$^2$.

By yet another aspect of the invention a method is provided for protecting from oxygen inhibition a radiation curable material that includes a polymerizable system including polymerizable organic compound, and polymerization initiator. The method includes preparing a liquid composition, forming a layer from the liquid composition present in an amount of at least about 35 mg/dm$^2$, and applying radiation to the radiation curable material through the layer.

DESCRIPTION OF THE PREFERRED EMBODIMENT

The present invention in its preferred form provides a method of ameliorating oxygen interference with curable materials having polymerizable systems containing polymerizable organic compound and polymerization initiator, expecially those systems that are polymerizable in response to actinic radiation and contain initiators that are activatable by actinic radiation and most especially those that are visible light curable. Such polymerizable systems present difficult problems in obtaining thorough cures having both good depth of cure and good surface cure. Obtaining good surface cure and depth of cure without oxygen inhibition is an especially severe problem when the materials being cured are shaped and have vertical surface, horizontal surface and crevice.

In its preferred form the present invention in its method involves preparing a liquid composition and applying the liquid composition to the vertical surface, horizontal surface and crevice of the material that is to be polymerized substantially excluding all air from the vertical surface, horizontal surface and crevice. The liquid composition is formed into a layer and thereafter radiation is applied to the polymerizable system through the layer.

As far as is known such a procedure has never been used with denture base materials or broadly even in the preparation of dental materials and especially those that are actinic light curable and even more significantly those that are visible light curable. In this regard, many preparations such as those shown in the prior art have been tried experimentally and found to be deficient in providing sufficient conditions of amelioration of the oxygen inhibition to prevent blanching and other deficiencies in a dental material which is to be exposed to the oral environment in the human mouth over a period of time, many years of use being expected. It has however, surprisingly been found that such objectives can be achieved if a liquid composition is prepared and applied in such proportions that a layer is provided present in an amount having a solids content of at least 35 mg/dm² on a fully dried basis, more preferably of 40 to 3000 mg/dm² and most preferably of 50 to 500 mg/dm².

The liquid composition is preferably an aqueous mixture including an organic compound with the preferred organic compound being an organic polymer that is water soluble and preferably one chosen from the group consisting of the polyvinyl pyrrolidones and the polyvinyl alcohols and mixtures thereof. The most preferable compounds are polyvinyl pyrrolidone and polyvinyl alcohol as contrasted to their copolymer and substituted polymers.

The organic compound is preferably present in the liquid composition in an amount of 6 to 70 percent by weight based on the weight of the liquid composition, more preferably in an amount of 7 to 50 percent and most preferably in an amount of 8 to 35 percent.

The liquid composition preferably has a viscosity of at least 40 cps, more preferably 50 to 50,000 cps and most preferably 50 to 500 cps.

Preferably the aqueous mixture contains a wetting agent. Examples of wetting agents are anionic, cationic and nonionic surfactants.

Preferred wetting agents are nonionic wetting agents such as the polyoxyethylenes, and by way of example, most preferably nonyl phenyl ethoxylate (containing 9 to 10 ethoxy groups). The wetting agent is preferably present in an amount of 0.01 to 3 percent, more preferably 0.1 to 3 percent by weight based on the weight of the polymer.

In addition to surfactants chain transfer agents may also be used such as those shown in U.S. Pat. No. 3,458,311, the contents of which are incorporated herein by reference. An example is triethylene glycol diacetate.

In addition to the above enumerated materials, other materials may also be present such as thickeners, colorants, pigmenting agents, stabilizers fillers and etc., so long as the amounts and properties of such other materials do not interfere with the passage of sufficient radiation to bring about the desired result.

Turning now to a consideration of the preferred substrate materials and especially the dental material that is filled and presents the most critical problem. One of the most difficult embodiments is a denture base having vertical surface, horizontal surface and crevice. Generally, crevices may have lengths of at least 1 mm, depths of at least 1 mm, and widths of no more than 0.5 mm.

The relatively vertical surfaces include the surfaces that are curved, offering portions that slope from the horizontal to the vertical to 45°. The relatively horizontal surfaces are those that progress toward the vertical up to 45°. Crevices are not only to be understood as folds but also areas along ridges of materials where the surfaces change angle fairly abruptly or have corners because these configurations can also be bridged by the coating that is to provide the protection from oxygen inhibition. It is generally preferable to use abrading application of the liquid coating in order to assure displacement of any air at the surface and provide good contact of the liquid with the surface. This abrading application with its resulting good contact of the surface by the liquid also assist in preventing reentry of air along the edges particularly at interfaces between teeth and denture base material. Preferably this application is provided by brushing or spraying. A special problem is presented in a crevice formed between the denture base material and a tooth, especially with the problem outlined above. Thus the abrading to remove the air is quite important in this regard for the preferred application of the present invention.

The preferred denture base materials are visible light curable and preferred for use of the present invention in the sense of the need for the present invention. Especially in need of the present invention are those denture based materials that are filled, containing fillers such as, inorganic and organic fillers. Examples of such fillers are the silaneous fillers and apatite, soda glass, quartz, silica gel, borosilicate glass, aluminum, metal fibers and polymer. These may be in the form of spheres, platelets, fibers, whiskers or may be irregularly shaped. The fillers may be present in quantities of 35 to 70 percent by volume of the denture base material or in more severe cases in amounts of 45 to 70 percent by volume of the denture base material. As a general consideration filler interferes with the passage of radiation. This is one criticality of the present invention.

The preferred polymerizable organic compound is ethylenically unsaturated and preferably is addition polymerizable and most preferably the acrylate monomers especially as shown in U.S. Serial No. 486,688 dated Apr. 26, 1983 which application is incorporated herein by reference. Preferably the organic compound is present in an amount of about 1 to about 99.9 percent by weight of the polymerizable system. The polymerizable system is made up of one or more of the following materials polymerizable organic compound or compounds, the initiator material and the accelerator material.

The preferred polymerization initiator compound is a radiation activatable compound. In some instances, a heat activatable initiator compound may also be included. More preferably, the radiation activatable compound is an actinic light activatable compound or photoinitiator. Such compounds are well-known, see, for example, U.S. Pat. No. 4,245,031, the contents of which are incorporated herein by reference.

Most preferably, the initiator is a visible light activatable compound making the polymerizable composition curable with visible light. The preferred class of initiators is the well-known diketones and the most preferred is camphoroquinone. Visible light activatable photoinitiators are discussed in U.S. Pat. No. 4,110,184, the contents of which are incorporated herein by reference.

The preferred accelerator is an organic amine. The most preferred accelerators are the organic amine salts that are the subject of Case 1508, Serial No. 486,688. The most preferred organic amine salts are those containing a tertiary amine moeity with a neopentyl acrylate radical and in which the amine salt is of an organic acid and the preferred acid is methacrylic acid.

The invention is further illustrated by the following examples:

EXAMPLE 1

A liquid composition was made by preparing a solution in a 16 oz. glass bottle at ambient conditions. The following materials were charged to the glass bottle:

180 g Aqueous solution of 37.5 % by weight of a polyvinyl pyrrolidone (Plasdone K-29/32) GAF Corp.)
30 g Water 1 g Aqueous solution of 0.1% by weight FD & C Red #40 Dye 10 g Aqueous solution of 1% by weight silicone antifoam (SAG 471 Union Carbide) and 5% by weight nonyl phenyl ethoxylate based wetting agent (Makon 10 Stepan Chemical Co.).

The resulting formula was obtained:
(1) 30.54%: Organic Compound
(2) 69.18%: Water
(3) 450 ppm: Dye
(4) 0.05%: Antifoam Agent
(5) 0.23%: Surfactant

EXAMPLE 2

1:1 mole ratio acid amine salt reaction product was formed by reacting 8.6 g of glacial methacrylic acid (MAA) and 15.7 g of dimethylaminoethyl methacrylate (DMAEMA) by combining these small quantities at room temperature in a 2 oz. amber glass container at room temperature and shaking them on a mechanical shaker for about one half hour and then letting stand for about one hour before using. The resulting amine salt DMAEMA-MAA was a clear, slightly viscous liquid.

EXAMPLE 3

A composition that is moldable to a denture base form and hardenable with visible light was prepared from the following ingredients:

Percent by Weight of Total Composition 39.44 Urethane dimethacrylate (Reaction product of hydroxyethyl methacrylate and 2,2,4-trimethylhexyl-1,6-diisocyanate)
2.57 1,6-Hexanediol dimethacrylate (HDDMA)
0.13 Camphoroquinone (CQ)
0.59 DMAEMA-MAA salt prepared as in Example 2
42.10 poly(methyl methacrylate-co-ethylene dimethacrylate 99.8:0.2) a polymer supplied by L. D. Caulk Co. (Polymer is in substantially spherical beads the shape resulting from its suspension polymerization. At least 50% by weight of the beads have average diameters of less than 50 microns. The polymer was prepared from methyl methacrylate and ethylene dimethacrylate by suspension polymerization*).
0.07 red acetate fibers
0.03 pigments
15.07 fumed silica inorganic filler (Aerosil R972 a product of Degussa).

*The polymer was prepared according to the teaching of U.S. Ser. No. 318,356, filed Nov. 5, 1981, which was a Continuation of U.S. Ser. No. 008,507, filed Feb. 1, 1977.

First CQ was dissolved in HDDMA and then mixed with the amine salt and urethane dimethacrylate. The resulting liquid solution was charged to a double planetary mixer heated to 45° C. and mixed under 20 mm Hg pressure. Next the polymer with the pigments and fibers previously blended in a V-Cone Blender was added and mixed under 20 mm pressure. The temperature was increased to 55° C. and the fumed silica was added in three increments of about equal size and mixed under 130 mm pressure each time. This produced a visible light curable (VLC) puttypaste.

The VLC putty was molded into a sheet 3.5"×2.5"×0.10" in a hydraulic press. The sheet was adapted as a baseplate to a stone model (coated with separator) made from an impression of the mouth. The baseplate was trimmed and then cured in two minutes on a turntable rotating under four 150 watt quartz-halogen lamps with a 400–500 nm band-pass filter. The light flux varied from 100–130 mw/cm$^2$ on the surface of the baseplate. Additional VLC putty was rolled into rope 0.25" in diameter. The rope was adapted around the ridge of the baseplate and a full arch of acrylic plastic teeth coated with a bonding agent was press-positioned in the rope. The teeth were further positioned in an articulator and then fixed in position by a two-minute light cure. Next the facial and lingual aspects of the denture were finished with additional rope.

The liquid composition of Example 1 was applied as a top coating before curing for a visible light curable denture resin. The surface after photocuring for 4 min. was dry, shiny and tack free. The denture was then removed from stone model and the other side of the denture was coated with the liquid/composition of Example 1 and then cured for 2 min. under the light. The surface was dry, shiny and tack free. Next, the cured denture was washed with tap water and dried with a paper towel. Both surfaces of the processed denture were shiny and tack free.

The denture that was processed with this anti-air-inhibition coating was immersed in boiling water for ten minutes, and dried in air. No blanching was observed. This indicates that the denture surfaces were completely polymerized.

As a reference, a similar denture processed without the anti-air-inhibition coating had dull and tacky surfaces. The denture exhibited severe blanching over all surfaces and was not clinically acceptable.

Blanching as used in this patent application is a whitening of the surface of the material after the completion of the polymerization procedure.

EXAMPLES 4–9

Examples 4–9 were carried out using denture base plates (the denture without teeth and supporting structure for the teeth) formed approximately as in Example 3. The liquid composition was prepared substantially as in Example 1, except as indicated. The blanch test was for 3 hours in boiling water.

TABLE I

| EX. | POLYVINYL PYRROLIDONE | WATER | WETTING AGENT | DYE | ANTI-FOAM | BLANCH | SURFACE GLOSS (SHINY) |
|---|---|---|---|---|---|---|---|
| 4 | 0 | 0 | 0 | 0 | 0 | Severe | No |
| 5 | 0 | 100% | 0 | 0 | 0 | Severe | No |
| 6 | 50 g (NP-K30GAF) Mol. wt. 40,000 | 50 g | .38 g Water Dispersible Poly Tergent S-205 LF Olin Chemical | 0 | 0 | None | Yes |
| 7 | 5 g (NP K90GAF) Mol. wt. 360,000 | 50 g | .28 g Water Dispersible Poly Tergent S-205 LF | 0 | 0 | None | Yes |

TABLE I-continued

| EX. | POLYVINYL PYRROLIDONE | WATER | WETTING AGENT | DYE | ANTI-FOAM | BLANCH | SURFACE GLOSS (SHINY) |
|---|---|---|---|---|---|---|---|
| 8 | 25 g (Plasdone K29/32GAF) Mol. wt. 40,000 | 50 g | Olin Chemical .38 g Water Dispersible Poly Tergent S-205 LF Olin Chemical | 0 | 0 | None | Yes |
| 9 | 23 g (Plasdone K26/28GAF) | 50 g | .31 g Water Dispersible Poly Tergent S-205 LF Olin Chemical | 0 | 0 | None | Yes |

EXAMPLES 10-24

Examples 10-24 were carrier out substantially as Examples 4-9 except as indicated in Table II:

ter. This is an indication of less degree of surface cure than those with polyvinyl pyrrolidone.

EXAMPLE 25

TABLE II

| Examples | Formulas | Nature of Polymers and Manufacturer | Consistency of Solution | Surface after Curing | Surface after Washing | Blanching after 3 hour boil |
|---|---|---|---|---|---|---|
| 10 | 1 g Kelcoloid HVF 60 g Water with 0.4% Makon 10 | A propylene glycol alginate from Kelco | very viscous | dry shiny | dry shiny | slight |
| 11 | 1 g Keltrol GFS 55 g Water with 0.4% Makon 10 | Xanthan Gum/ Galactomannans Blend from Kelco | very viscous | dry shiny | dry shiny | slight |
| 12 | 1 g Kelcoloid S 40 g Water with 0.4% Makon 10 | A propylene glycol alginate from Kelco | viscous | dry shiny | dry shiny | slight |
| 13 | 1 g Keltose 80 g Water with 0.4% Makon 10 | An ammonium calcium alginate from Kelco | very viscous | dry shiny | dry shiny | moderate |
| 14 | 2 g Klucel LF 50 g Water with 0.4% Makon 10 | A hydroxypropyl cellulose from Hercules, Inc. | slightly viscous | dry dull | dry shiny | moderate |
| 15 | 2 g Natrosol 250 HR 85 g Water with 0.4% Makon 10 | A hydroxyethyl cellulose from Hercules, Inc. | very viscous | dry dull | dry shiny | severe |
| 16 | 1 g Klucel HF 73 g Water with 0.4% Makon 10 | A hydroxypropyl cellulose from Hercules, Inc. | very viscous | dry dull | dry shiny | severe |
| 17 | 1.5 g Culminal MHEC 20,000 PR 50 g Water with 0.4% Makon 10 | A methylhydroxyethyl cellulose from Henkel Corp. | very viscous | dry dull | dry shiny | severe |
| 18 | 1 g Cellosize Qp-300 50 g Water with 0.4% Makon 10 | A hydroxyethyl cellulose from Union Carbide Corp. | slightly viscous | dry shiny | dry shiny | slight |
| 19 | 1 g Culminal MC 4000PS 75 g Water with 0.4% Makon 10 | A methyl cellulose from Henkel Corp. | very viscous | dry dull | dry dull | moderate |
| Examples | Formulas | Nature of Polymers and Manufacturer | Consistency after Curing | Surface after Curing | Surface after Washing | Blanching after 3 hour boil |
| 20 | 1 g Culminal MHPC 20,000P 70 g Water with 0.4% Makon 10 | A methyl hydroxy-propyl cellulose from Henkel Corp. | very viscous | dry dull | dry dull | moderate |
| 21 | 70 g Carbowax 1450 40 g Water with 0.5% Poly Tergent S-205LF | A polyethylene glycol ether from Union Carbide | slightly viscous | surface whiteness no good | tack free, white surface | not tested |
| 22 | 50 g Carbowax 3350 55 g Water with 0.5% Poly Tergent S-205LF | A polyethylene glycol ether from Union Carbide | slightly viscous | surface whiteness no good | tack free, white surface | not tested |
| 23 | 50 g Carbowax 8000 80 g Water with 0.5% Poly Tergent S-205LF | A polyethylene glycol ether from Union Carbide | slightly viscous | surface whiteness no good | tack free, white surface | not tested |
| 24 | Control - no solution on top of curing surface | — | — | wet, shiny, very tacky | dull, very tacky | severe |

Table II shows the efficacy of various water soluble polymers evaluated for use in the oxygen barrier coatings. All of these offered better surface cure than the control of Example 24 which did not have the coating. However, none of these coatings produced cured surface totally blanch free after a 3 hour boil cycle in wa- The composition of Example VII of U.S. Pat. No. 3,458,311 was prepared as follows:

An aqueous solution was prepared by dissolving and mixing the following ingredients together:

3.00 g Vinol 523, a medium viscosity, partially hydrolyzed polyvinyl alcohol manufactured by Air Products and Chemicals Inc. (87-89% hydrolysis, viscosity 22-26 centipoises in 4% aqueous solution at 20° C.)

0.06 g Alkasurf OP-10, an octyl phenol ethoxylate surfactant (wetting agent) manufactured by Alkaril Chemicals, Inc., having the following formula

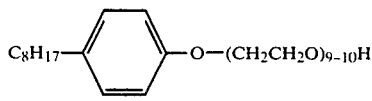

96.94 g Water.

The resulting solution was a fairly fluid liquid as measured with a Brookfield Synchro-lectric Viscometer (Model RVT with measuring range of 0 to 8 million centipoises (cps)) having a viscosity of 30 centipoises (cps) (#3 spindle, 100 rpm) at 22° C.

The resulting solution was tested as follows:

A rectangular flat baseplate of a visible light curable (VLC) denture base resin measuring about 6 cm×5 cm×0.2 cm was cut and placed on a clear cellophane film. The VLC resin was a pink doughy mass consisting of an urethane acrylate, 1,6 Hexanediol dimethacrylate diluent, acrylic polymer beads, fumed silica filler, camphoroquinone (initiator), Dimethylaminoneopentyl acrylate - methacrylic acid salt (accelerator), pigments and thermal stabilizers prepared substantially as described in Example 3.

The baseplate was weighed to the fourth decimal using an analytical balance. A uniform layer of the above aqueous coating was coated onto the top surface of the baseplate and immediately weighed again to obtain the net wet coating weight. The wet coated baseplate was then exposed for 5 min. at a distance of 18 cm under four 150 w. quartz-halogen lamps. The exposure unit had a built-in fan for air circulation in order to reduce heat build-up inside the curing chamber.

After the 5 min. visible light curing, the top surface had a waxy feel. The cured baseplate was washed with tap water and then placed in boiling water for 10 min. Severe top surface blanching was observed. Seven additional samples were prepared and the procedure was repeated, except that the coating weight was varied on purpose. All showed severe top surface blanching. The bottom surface in contact with the cellophane film did not show any blanching at all.

The wet coating weights were converted into net solid weight by multiplying with the percentage of the polymer in the solution and then divided by the surface area. It was found that the solid polymer coating weights were 5.3, 7.7, 10.0, 11.3, 16.0, 17.0, 19.0 and 35.3 mg/dm$^2$.

EXAMPLE 26

The composition of Example XVIII of U.S. Pat. No. 3,458,311 was prepared as follows:

A coating solution was prepared by dissolving and mixing the following ingredients:
6.00 g Vinol 523
0.12 g Alkasurf OP-10 (2% based on the weight of solid Polymer)
93.88 g Water.

The resulting solution has a Brookfield viscosity of 119 cps (#4 spindle, 100 rpm) at 22° C.

The solution was applied onto the denture base and tested as described in Example 25. The relationship between the dry coating weight and surface blanching was as follows:

| Weight of PVA (mg/dm$^2$)* | Surface Blanching |
| --- | --- |
| 20.3 | Moderate |
| 24.3 | Slight |
| 36.7 | None |
| 44.3 | None |
| 53.0 | None |
| 57.0 | None |
| 80.0 | None |
| 105.0 | None |

*includes the wetting agent solids.

EXAMPLE 27

The composition of Example XXI of U.S. Pat. No. 3,458,311 was prepared as follows:

A coating solution was prepared by dissolving and mixing the following ingredients:
6.00 g Plasdone K 29/32, a polyvinyl pyrrolidone with average molecular weight of 40,000 manufactured by GAF Corp.
0.12 g Alkasurf OP-10 (2% based on the weight of solid polymer)
93.88 g Water.

The resulting solution was a very fluid liquid with a Brookfield viscosity of 16 cps (#3 spindle, 100 rpm) at 22° C.

The solution was applied onto the denture resin and tested as described in Example 25. The dry coating weights mg/dm$^2$) were 12.0, 15.0, 16.0, 16.3, 25.7, 29.0, 30.0 and 34.3. All samples showed severe surface blanching after 10 min. in boiling water.

EXAMPLE 28

A coating solution was prepared by dissolving and mixing the following ingredients:
9.08 g Vinol 523
0.18 g Alkasurf OP-10 (2% based on the weight of solid polymer)
90.74 g Water.

The resulting solution was a viscous liquid, with a Brookfield viscosity of 636 cps (#4 spindle, 100 rpm) at 22° C.

The solution was applied and tested as described in Example 25 to a denture resin. The relationship between the dry coating weight and the surface blanching was as follows:

| PVA (mg/dm$^2$) | Surface Blanching |
| --- | --- |
| 41.0 | Slight |
| 56.3 | None |
| 89.6 | None |
| 105.0 | None |
| 113.0 | None |
| 117.3 | None |
| 145.0 | None |
| 240.0 | None |

EXAMPLE 29

A coating solution was prepared by dissolving and mixing the following ingredients:
20.0 g Vinol 523
0.4 g Alkasurf OP-10
79.6 g Water.

The resulting solution was a very viscous liquid, with a Brookfield viscosity of 50,533 cps (#4 spindle, 2.5 rpm) at 22° C.

The coating was applied and tested in Example 25. The dry coating weights were 341.0, 568.7, 758.0 and 940.7 mg/dm$^2$ respectively.

No surface blanching was observed.

EXAMPLE 30

A coating solution was prepared by dissolving and mixing the following ingredients:
18.25 g Plasdone K 29/32
0.37 g Alkasurf OP-10
81.38 g Water.

The resulting coating was a fairly fluid liquid with a Brookfield viscosity of 49 cps (#3 spindle, 100 rpm) at 22° C.

The coating was applied and tested in Example 25. The relationship between dry coating weights and the surface blanching was as follows:

| PVP (mg/dm$^2$) | Surface Blanching |
| --- | --- |
| 37.0 | Severe |
| 44.3 | Severe |
| 50.0 | Severe |
| 80.0 | Moderate |
| 91.7 | Slight |
| 124.0 | None |
| 135.7 | None |
| 306.0 | None |

EXAMPLE 31

The procedure of Example 30 was repeated with a solution of:
30.50 g Plasdone K 29/32
0.61 g Alkasurf OP-10 (2% by weight of solid polymer)
68.89 g Water.

The slightly viscous solution had a Brookfield viscosity of 170 cps (#4 spindle, 100 rpm). The dry coating weights were 195.0, 251.7, 344.7 and 384.0 mg/dm$^2$. All samples were free from surface blanching after 10 min. in boiling water.

EXAMPLE 32

The procedure of Example 30 was repeated with a solution of:
52.38 g Plasdone K 29/32
0.95 g Alkasurf OP-10 (2% by weight of solid polymer)
46.67 g Water.

The solution was very viscous and had a Brookfield viscosity of 8,508 cps (#4 spindle, 20 rpm). The dry coating weights were 580.0, 1329.7, 1864.7 and 2578.0 mg/dm$^2$. No surface blanching was observed.

EXAMPLES 33-36

The following examples demonstrate the effect of the polymer concentration on the blanch resistance of a cured denture.

A master stock solution was prepared by dissolving and mixing the following ingredients:
68.64 pbw Deionized water 0.45 0.1% FD & C Red #40 Dye in Water
0.045 SAG 471, a silicone antifoam (Union Carbide)
0.225 Makon 10, a nonyl phenol ethoxylate surfactant (Stepan Chemical)
0.50 Sodium Benzoate, a preservative.

Polyvinyl pyrrolidone (Plasdone K 29/32) was dissolved in this master stock solution to produce solutions containing 30.5%, 15.2%, 7.6% and 3.8% Plasdone K 29/32. These solutions were applied to denture base resins as described in Example 25 and tested as described in Example 25. The relationship between the dry polymer coating weights and the surface blanching was found as follows:

| EX. | PVP CONC. IN SOLUTION | DRY PVP WEIGHT (mg/dm$^2$) | SURFACE BLANCHING |
| --- | --- | --- | --- |
| 33 | 3.8% | 4.1 | Severe |
| | | 5.9 | Severe |
| | | 6.6 | Severe |
| | | 9.0 | Severe |
| 34 | 7.6% | 10.2 | Severe |
| | | 10.8 | Severe |
| | | 12.9 | Severe |
| | | 14.1 | Severe |
| 35 | 15.2% | 19.4 | Severe |
| | | 20.2 | Severe |
| | | 31.1 | Severe |
| | | 42.8 | Moderate |
| 36 | 30.5% | 65.0 | None |
| | | 68.8 | None |
| | | 96.9 | None |
| | | 116.7 | None |
| | | 177.5 | None |
| | | 223.0 | None |
| | | 249.3 | None |
| | | 387.8 | None |

Examples 25-36 are believed to indicate:

1. The 2-30 mg/dm$^2$ coverage suggested in U.S. Pat. No. 3,458,311 is not usable for the technology of the present invention.

2. To produce blanch resistant surface by the technology of the present invention, the minimum solid coating weight is about 35 mg/dm$^2$ for polyvinyl alcohol and 60 mg/dm$^2$ for polyvinyl pyrrolidone in preferred applications. The maximum coating weight for practical application is about 3000 mg/dm$^2$ in preferred applications.

3. In contrast to the preferred 3-6% polymer concentrations suggested in U.S. Pat. Nos. 3,458,311 and 4,072,528, the preferred polymer concentrations of the present invention are 6-20% for polyvinyl alcohol, and 18-50% for polyvinyl pyrrolidone.

The present invention provides the following advantages over the previously known methods of controlling air inhibition:

1. The coating is easily applied and conforms readily to any contour surface.

2. No waiting time is necessary.

3. Compressed gas cylinders and valves are unnecessary.

4. The coating improves substrate properties, while integral blends of solvents, plasticizers and waxes may degrade physical and chemical properties.

5. The coating is non-toxic.

6. The substrate from which the coating is washed is non-toxic.

7. A glossy hard surface is obtained.

8. The substrate formed using the coating is stronger and chemically resistant to extraction and thereby is of low toxicity. The substrate thus formed is also resistant to staining and absorption of odor causing substances.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

It is claimed:

1. A method of preparing a shaped dental prosthetic device for use in a human mouth comprising:
   (1) shaping a curable dental material into a shaped dental prosthetic device having at least two surfaces approximately perpendicular to each other, positioning said device so that one of said surfaces is substantially vertical and the other of said surfaces is substantially horizontal; said material including a polymerization initiator for said substance activatable by visible light in the range of about 400-500 nm;
   (2) coating said surfaces with a liquid composition which will substantially exclude air from said surfaces; said composition comprising;
      (a) an organic compound present in an amount of about 6 percent or more, based on the weight of said liquid composition, and
      (b) having a viscosity of about 50 to about 50,000 cps said liquid composition being applied to both the substantially vertical surface and the substantially horizontal surface of said dental members in a residentual layer of at least about 35 mg/dm$^2$ on a fully dry weight basis; and
   (3) applying visible light radiation of about 400 to about 500 nm to the substantially vertical surface and to the substantially horizontal surface of the device through said composition.

2. The method of claim 1 wherein said liquid composition comprising a surfactant, said organic compound is water soluble and present in an amount of about 6 to about 70 percent by weight based on the weight of said liquid composition, said liquid composition being an aqueous mixture; and said layer present in a amount of about 40 to about 3000 mg/dm$^2$ on a fully dried weight basis.

3. The method of claim 2 wherein said curable dental material is a denture base material, visible light curable, comprising filler present in an amount of about 35 to about 70 percent by volume of said denture base material; and said polymerizable organic compound is ethylenically unsaturated and present in an amount of about 1 to about 99.9 percent by weight of said polymerizable system and said denture base material containing at least one tooth projecting therefrom; and said organic compound is a polymer present in said liquid composition in an amount of about 7 to about 50 percent by weight based on the weight of said liquid composition.

4. The method of claim 3 wherein said polymerizable system comprising an accelerator, said initiator comprising diketone, said ethylenically unsaturated compound comprising acrylate monomer, said filler is present in an amount of about 45 to about 70 percent by volume of said denture base material, said organic compound comprising polymer chosen from the group consisting of polyvinyl pyrrolidones and polyvinyl alcohols and mixtures thereof present in an amount of about 8 to about 35 percent by weight based on the weight of said liquid composition and said liquid composition comprising 0.01 to 3 percent wetting agent by weight based on the weight of said polymer, and said layer being solid and present in an amount about 50 to about 500 mg/dm$^2$ on a fully dried weight basis.

5. The method of claim 1 wherein said light exposure is for three minutes at 132 mw/cm$^2$ of visible light supplied by a 150 watt quartz halogen lamp with a 400-500 nm band-pass filter; and whereby said dental member is upon being submerged in boiling water for 10 minutes and then removed and dried, substantially free of visible surface blanch, whereas the dental material treated with the same method without said liquid composition is observably substantially more blanched.

6. The method of claim 5 wherein said member contains a crevice with a length of at least 1 mm, a depth of at least 1 mm and a width of no more than ½ mm.

7. The method of claim 1 wherein said light exposure is for three minutes at 132 mw/cm$^2$ of visible light supplied by a 150 watt quartz halogen lamp with a 400-500 nm band-pass filter, and whereby said dental member is upon being submerged in boiling water for 10 minutes and then removed and dried, substantially free of visible surface blanch, whereas the dental material is treated with the same method without said liquid composition is observably substantially more blanched.

* * * * *